(12) United States Patent
DeMello et al.

(10) Patent No.: US 6,695,836 B1
(45) Date of Patent: Feb. 24, 2004

(54) DEVICE AND METHOD FOR MYOCARDIAL REVASCULARIZATION

(75) Inventors: Richard M. DeMello, Acton, MA (US); Maureen A. Finlayson, Acton, MA (US)

(73) Assignee: Radius Medical Technologies, Inc., Acton, MA (US)

( * ) Notice: Subject to any disclaimer, the term of this patent is extended or adjusted under 35 U.S.C. 154(b) by 82 days.

(21) Appl. No.: 09/609,410

(22) Filed: Jul. 3, 2000

(51) Int. Cl.⁷ .............................................. A61B 18/04
(52) U.S. Cl. .............................. 606/28; 606/27; 606/29
(58) Field of Search .................... 606/27–29, 31–34, 606/41, 42, 45–50; 607/101, 102, 98

(56) References Cited

U.S. PATENT DOCUMENTS

| | | | | |
|---|---|---|---|---|
| 4,269,174 A | * | 5/1981 | Adair | 606/40 |
| 4,658,817 A | * | 4/1987 | Hardy | 219/121.7 |
| 4,920,982 A | * | 5/1990 | Goldstein | 606/40 |
| 5,122,137 A | * | 6/1992 | Lennox | 606/40 |
| 5,403,311 A | * | 4/1995 | Abele et al. | 606/49 |
| 5,514,131 A | * | 5/1996 | Edwards et al. | 606/45 |
| 5,522,815 A | * | 6/1996 | Durgin, Jr. et al. | 606/50 |
| 5,800,428 A | * | 9/1998 | Nelson et al. | 606/41 |
| 5,807,395 A | * | 9/1998 | Mulier et al. | 606/41 |
| 5,925,012 A | * | 7/1999 | Murphy-Chutorian et al. | 604/20 |
| 5,951,546 A | * | 9/1999 | Lorentzen | 606/41 |
| 5,964,754 A | * | 10/1999 | Osypka | 606/37 |
| 6,030,380 A | * | 2/2000 | Auth et al. | 128/898 |
| 6,053,911 A | | 4/2000 | Ryan et al. | |
| 6,106,520 A | * | 8/2000 | Laufer et al. | 606/32 |
| 6,156,031 A | * | 12/2000 | Aita et al. | 604/114 |
| 6,176,856 B1 | * | 1/2001 | Jandak et al. | 606/29 |
| 6,224,566 B1 | * | 5/2001 | Loeb | 604/20 |
| 6,286,512 B1 | * | 9/2001 | Loeb et al. | 128/898 |
| 6,287,297 B1 | * | 9/2001 | Woodruff et al. | 128/898 |

FOREIGN PATENT DOCUMENTS

| | | |
|---|---|---|
| WO | WO 97/18768 | 5/1997 |
| WO | WO 99/44523 | 9/1999 |
| WO | WO 00/18308 | 4/2000 |

* cited by examiner

*Primary Examiner*—Roy D. Gibson
(74) *Attorney, Agent, or Firm*—Cesari and McKenna, LLP (57) ABSTRACT

A device and method for treating tissue at a treatment site. The device and method include supplying controlled energy to a heating portion of the device positioned within a tissue wall at the treatment site. The size of the heating portion and energy supplied provides for ablation of the tissue to form a cavity within the tissue wall without ablating the surfaces of the tissue wall. Treatment fluid can then be supplied through the device to the cavity to supplement growth of blood vessels or retard such growth at the treatment site. The device can also be used to create an injury zone at a treatment site without ablating tissue, wherein the injury zone can be injected with treatment fluid. The device and method has use anywhere within the body, especially in the regions of the heart.

21 Claims, 6 Drawing Sheets

DEVICE AND METHOD FOR MYOCARDIAL REVASCULARIZATION

BACKGROUND OF THE INVENTION

1. Field of the Invention

This invention relates to a device and method for treating tissue at a treatment site within the body of a patient, and more particularly to a device and method for promoting myocardial revascularization in a patient.

2. Background of the Invention

A large variety of medical devices and methods have been utilized for treating cardiovascular disease. Many minimally invasive alternatives to conventional procedures such as open heart surgery or cardiovascular bypass surgery for treating heart disease have been developed. Myocardial revascularization is one such minimally-invasive procedure for treating heart disease that avoids the complications that can arise in conventional approaches requiring median sternotomy.

Myocardial revascularization is indicated when the coronary arteries that deliver the heart's own blood supply become clogged, thereby causing the muscle wall of the heart to be starved of oxygen. Present techniques for myocardial revascularization involve the removal of tissue from the heart wall in the area starved of oxygen, and creating channels though the endocardium into the myocardium. Such present techniques have been successful in promoting the formation of new blood vessels within the myocardium and thereby improving blood perfusion at or near the treatment site.

It was originally believed that the success of the present myocardial revascularization techniques was attributable to the fact that the channels formed in the heart wall remained open, and thus fed blood directly from the interior of the heart into the channels. It has been determined through several independent studies however, that these channels do not remain open for an extended period of time. Experts now believe that the trauma to the to the heart wall sustained during the creation of the channels is responsible for promoting new blood vessels surrounding the treatment site. These new blood vessels subsequently help to supply oxygenated blood to the otherwise underperfused region.

Methods for creating the channels in the heart wall include the use of laser energy, radiofrequency energy, ultrasonic energy, water jet drilling, and mechanical coring. Laser, radiofrequency, and ultrasonic energy methods have the added benefit of creating a thermal trauma to the heart wall while ablating the tissue of the heart.

A second method for stimulating new blood vessel growth involves injecting DNA or protein-based growth factors into the body. Several methods under investigation include systemic, intracoronary, epicardial, endocardial, and intramyocardial injections. It is believed that the most desirable method for injection is intramyocardial delivery. This method provides for drug delivery directly to the site in the heart where new blood vessel growth is desired while avoiding potentially undesirable effects in other regions of the body.

Several studies also suggest that creating an injury at a treatment site produces an increased propensity for the tissue to accept certain growth factors at the treatment sites. It is thus believed that the combination of forming the channels within the heart wall and subsequently infusing growth factor drugs into the treatment sites has advantages over either of the methods by themselves. The combination of injecting neovascularizing growth factors directly into the injury zone surrounding the treatment site can potentially have the greatest positive outcome over all other methods of myocardial revascularization. Present methods for performing the combined procedure involve removing or ablating tissue from the heart wall via thermal or mechanical means and then injecting growth factors either directly into the channel or adjacent to the channel site.

A problem exists, however, in attempting to combine thermal ablation and infusion procedures. After a channel is created in the heart wall and a growth factor is deposited or injected into the channel, a majority of the growth factor will not remain within the heart wall to perform its intended purpose. Unfortunately, the growth factor is squeezed from the open channel and washed away into the blood stream due to the high contractility of the heart wall during systole.

SUMMARY OF THE INVENTION

The advantages and purposes of the invention will be set forth in part in the description which follows, and in part will be obvious from the description, or may be learned by practice of the invention. These advantages and purposes will be realized and attained by way of the elements and combinations particularly pointed out in the appended claims.

To attain the advantages and in accordance with the purpose of the invention, as embodied and broadly described herein, the invention is directed to a treatment device for body tissue comprising a proximal end assembly including a controller and energy generator and a distal end assembly connected to the proximal end assembly through a body portion. The distal end assembly including a heating portion located distal of a nonconductive portion, the heating portion being operably connected to the controller and energy generator to receive controlled energy therefrom, and the heating portion and nonconductive portion of the distal end assembly are sized so that the heating portion, when inserted into the myocardium of a human heart, is completely located between the epicardium and endocardium, and the nonconductive portion extends through one of the epicardium and endocardium, such that said energy supplied to the heating portion ablates myocardium tissue to form a cavity therein without ablating the epicardium or endocardium.

In accordance with another aspect, the present invention comprises a treatment device for use with body tissue comprising a proximal end assembly including a controller, energy generator and injection assembly and a distal end assembly connected to the proximal assembly through a body portion. The distal end assembly including a heating portion operably connected to the controller and energy generator to receive controlled energy therefrom, and the injection assembly being fluidly connected to the distal end assembly so as to allow fluid to be injected to and through the distal end assembly.

In accordance with yet another aspect, the present invention comprises a method for treating tissue within a body comprising the steps of inserting a distal end assembly of a tissue treatment device into a tissue wall of the body, and forming a cavity completely within surfaces of said tissue wall by supplying controlled energy to a heating portion of the distal end assembly, the energy supplied being sufficient to ablate tissue between the surfaces without ablating a surface of the tissue wall.

In accordance with another aspect, the present invention comprises a method for treating tissue within a body comprising the steps of inserting a distal end assembly of a tissue treatment device into a tissue wall of the body, supplying controlled energy to a heating portion of the distal end assembly to heat the tissue wall, and injecting a treatment fluid from a proximal end of the tissue treatment device through the distal end assembly and into the tissue wall.

BRIEF DESCRIPTION OF THE DRAWINGS

The accompanying drawings, which are incorporated in and constitute a part of this specification, illustrate several embodiments of the invention and together with the description serve to explain the principles of the invention. In the drawings.

DETAILED DESCRIPTION OF THE PREFERRED EMBODIMENT

Reference will now be made in detail to the invention, examples of which are illustrated in the accompanying drawings. The same reference numbers may be used throughout the drawings to refer to the same or like parts.

The device and method of the present invention will generally be described in connection with performing myocardial revascularization on a patient. The present invention, however, has utility in a wide variety of medical procedures, including promoting blood vessel growth body tissue other than the heart, or even retarding the growth of certain diseased tissue or tumors.

Figure 1:
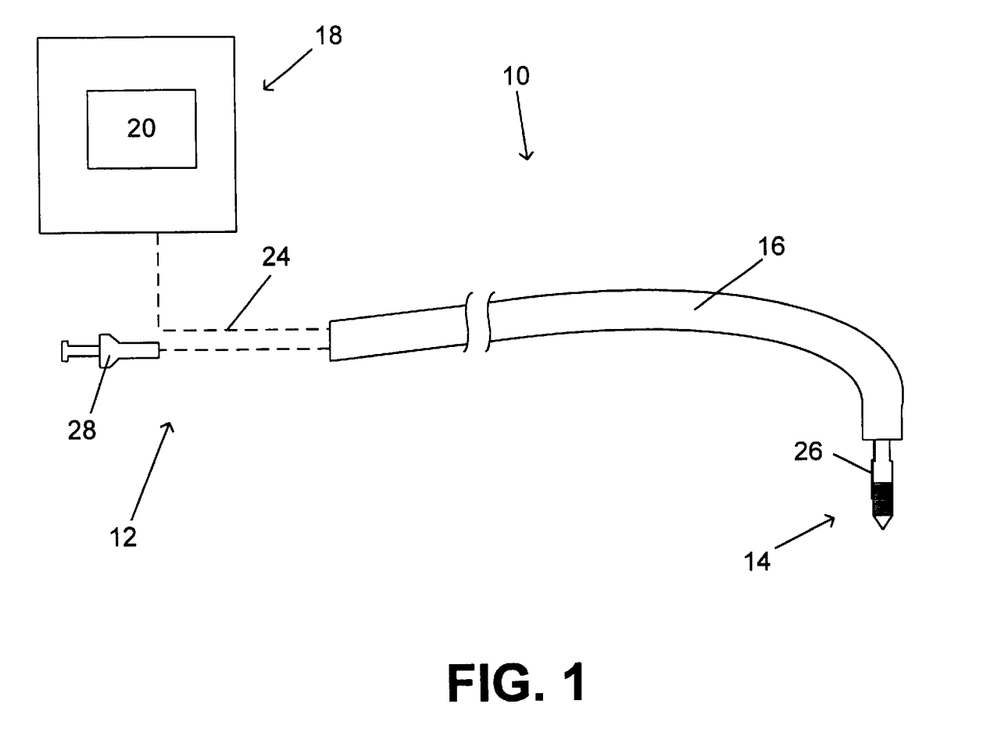
FIG. 1 illustrates a tissue treatment device according to the present invention.

FIG. 1 illustrates a tissue treatment device as a hollow guidewire system 10 according to the present invention. Hollow guidewire system 10 includes a proximal end assembly 12, a distal end assembly 14, and a hollow guidewire body 16 located between proximal end assembly 12 and distal end assembly 14. According to the present invention, distal end assembly 14 and portions of guidewire body 16 are designed to be insertable into a patient's body for positioning adjacent a treatment site. Distal end assembly 14 of guidewire system 10 will be discussed in more detail below.

Proximal end assembly 12 of guidewire system 10 includes a controller 18 having a radiofrequency wave form generator 22. Controller 18 may include a microprocessor to further assist the system in interpreting and relaying the required signals of the system. Controller 18 with generator 22 heat distal end assembly 14 by supplying controlled radiofrequency energy from controller 18 through an output line 24 to guidewire body 16. The energy then travels through guidewire body 16 to distal end assembly 14. According to an illustrative embodiment of the present invention, distal end assembly 14 forms an integral part of guidewire body 16 so that the energy from generator 22 travels directly from guidewire body 16 to distal end assembly 14. Alternatively, however, energy from generator 22 could travel along a conductive line running within or along (but separate from) guidewire body 16 and connected to distal end assembly 14.

Controller 18 may be of any suitable configuration used to deliver controlled radiofrequency energy to distal end assembly 14 of guidewire system 10. Several examples of suitable controller configurations are described in U.S. Pat. No. 5,743,900 to Hara, the disclosure of which is incorporated herein by reference. As fully described in the patent to Hara, controller 18 of the present invention may be connected to a thermocouple 26 fixed at distal end assembly 14 to monitor the temperature of distal end assembly 14. Further, suitable monitoring configurations as disclosed in the Hara patent may be included in controller 18 to determine and maintain optimal heating of distal end assembly 14. In addition, controller 18 may include a mapping or navigation system for assisting the operator in directing distal end assembly 14 to the desired location within the patient. Examples of such a mapping or navigation system can be found in U.S. Pat. No. 5,443,489 to Ben-Haim and U.S. Pat. No. 5,769,843 to Abela et al. Both the Ben-Haim and Abela et al. patents are herein incorporated by reference.

Proximal end assembly 12 of guidewire system 10 also includes an injection assembly 28 for delivering treatment fluid, such as growth factor drugs, from proximal end assembly 12, through hollow guidewire body 16, to distal end assembly 14. Injection assembly 28 may be formed in any standard configuration. For example, injection assembly 28 may include a syringe mechanism in fluid sealed communication with the lumen of hollow guidewire body 16. Consistent with the present invention, hollow guidewire body 16 may be replaced with a non-hollow guidewire body. When utilizing a non-hollow guidewire body, treatment fluid can be delivered from proximal end assembly 12 to distal end assembly 14 through a lumen attached to the non-hollow guidewire.

Guidewire body 16 may be formed of any suitable electrically conductive material with sufficient columnar strength to be urged through body cavities, yet flexible enough to locate distal end assembly 14 at a wide variety of treatment sites. For example, hollow guidewire body 16 may be formed of stainless steel or nickel-titanium alloys. As mentioned above, alternatively a conductive line separate from guidewire body 16 could transfer the energy to distal end assembly 14. With this alternative configuration, guidewire body may be formed from a non-conductive material, such as polyamide or urethane.

Figure 2:
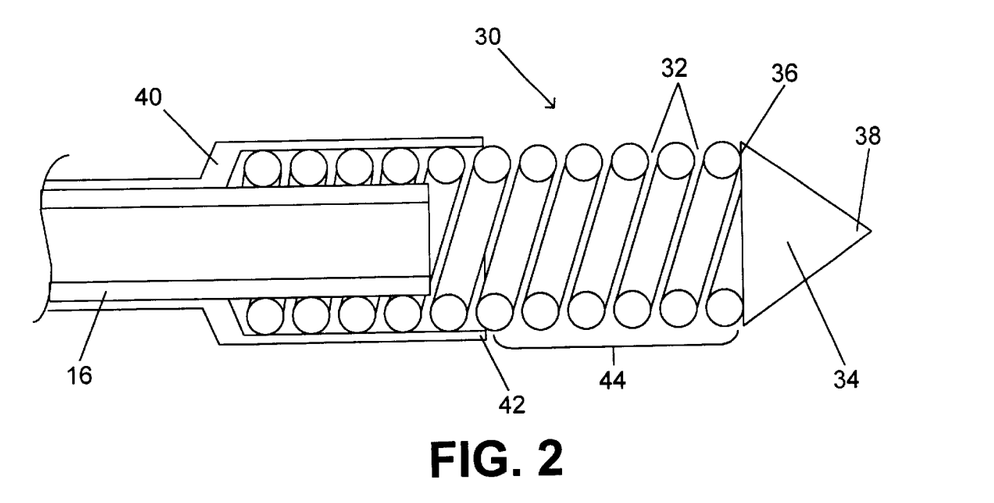
FIG. 2 is a cross-sectional enlarged view of the distal end assembly of the tissue treatment device of FIG. 1.

FIG. 2 illustrates the present preferred embodiment of distal end assembly 14 of guidewire system 10. Distal end assembly 14 includes a heating element 30 formed in the shape of a coil spring integral with a distal end of a hollow guidewire body 16. The coil spring configuration of heating element 30 includes gaps or exit areas 32 between individual turns of the coil. Treatment fluid, such as a growth factor drug, can delivered through hollow guidewire body 16, flow through gaps 32 of heating element 30, and exit the system at the desired treatment site. Heating element 30 may be formed of any suitable conductive material, for example platinum, stainless steel, gold, silver, or nickel-titanium alloys.

A rigid end element 34 is formed or fixedly secured to the distal end 36 of heating element 30. End element 34 may be formed in any suitable shape as long as it allows for penetration into the tissue wall of a treatment site. According to one illustrative embodiment, end element 34 is formed in a conical shape having a pointed or needle-like tip 38. Alternative shapes include a multi-faceted pyramid shaped configuration or a hollow point configuration. End element 34 may be formed of any rigid material and is preferably capable of conducting at least a portion of the radiofrequency energy flowing through heating element 30. According to one illustrative embodiment, end element is formed by sealing the end of heating element 30 with conductive solder or braze, and grinding the solder or braze to a needle-like point. Alternatively, end element 34 may be formed of stainless steel, aluminum, silver, gold, platinum, or nickel-titanium alloys.

Guidewire body 16 and proximal portions of distal end assembly 14 are covered about their circumference with a thin nonconductive sleeve 40. Nonconductive sleeve 40 may be formed of any appropriate material, for example polyamide or PTFE tubing. Sleeve 40 serves the dual purpose of (1) assisting smooth travel of guidewire body 16 though the various cavities of the patient's body, and (2) forming a nonconductive portion of distal end assembly 14 insulating portions of heating element 30 so as to define a proximal boundary 42 of a heating portion 44 of heating element 30.

According to the preferred embodiment, sleeve 40 covers guidewire body 16 and extends over distal end assembly 14 so that heating portion 44 extends approximately 2 mm along the distal-most portion of heating element 30. In an alternative embodiment (not shown), sleeve 40 may not be included over guidewire body 16, but only cover a small portion of distal end assembly 14. In this alternative embodiment, sleeve 40 would extend in a proximal direction for at least approximately 2 mm along the distal end assembly 14 starting at a distance approximately 2 mm from the distal-most portion of heating element 30. Consistent with the preferred sleeve configuration illustrated in FIG. 2, and the alternative design, sleeve 40 defines proximal boundary 42 of an approximately 2 mm long exposed or heating portion 44 of heating element 30. Exposed or heating portion 44 allows conduction of radiofrequency energy from controller 18 to the treatment site.

Figure 3:
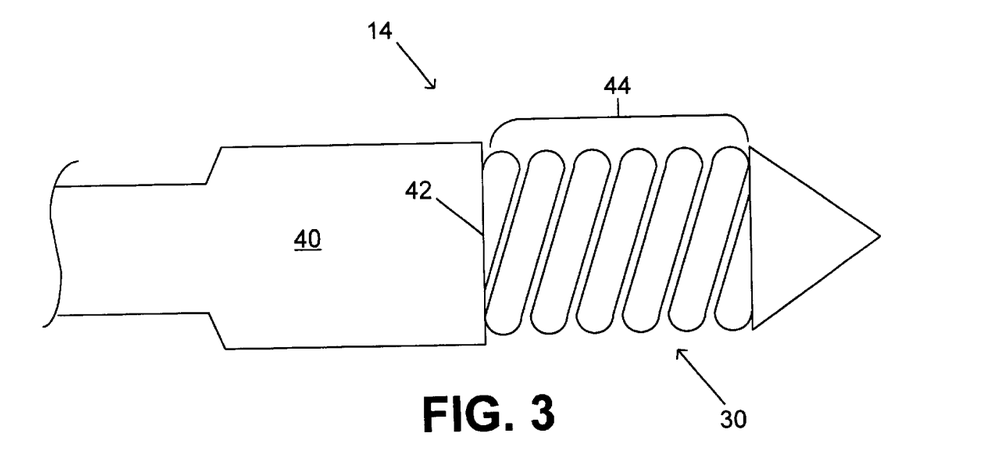
FIG. 3 is an elevational view of the distal end assembly of the tissue treatment device of FIG. 1.

FIG. 3 is an elevational view of distal end assembly 14 of hollow guidewire system 10. In this view, the exposed or heating portion 44 of heating element 30 is clearly depicted. Nonconductive sleeve 40 extends proximally from boundary 42, thereby forming the approximately 2 mm long exposed or heating portion 44.

Figure 4A:
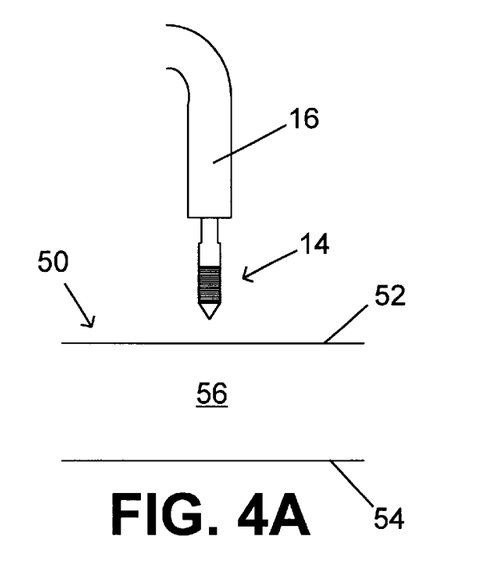
FIGS. 4A–4E illustrate the method steps of myocardial revascularization using the tissue treatment device of FIG. 1 according to the present invention.

FIGS. 4A through 4E illustrate a first method for performing myocardial revascularization in accordance with the present invention. FIG. 4A illustrates distal end assembly 14 of the hollow guidewire system 10 located adjacent a treatment site before the myocardial revascularization procedure is initiated. Reference character 50 points to a heart wall of a patient at a desired treatment site. Depending upon the desired location of distal end assembly 14, either outside or within the heart, surface 52 of heart wall 50 may be either the epicardium or the endocardium. Conversely, surface 54 would represent the other of the epicardium or the endocardium. The myocardium 56 is located between surfaces 52 and 54 of the heart wall 50.

Figure 4B:
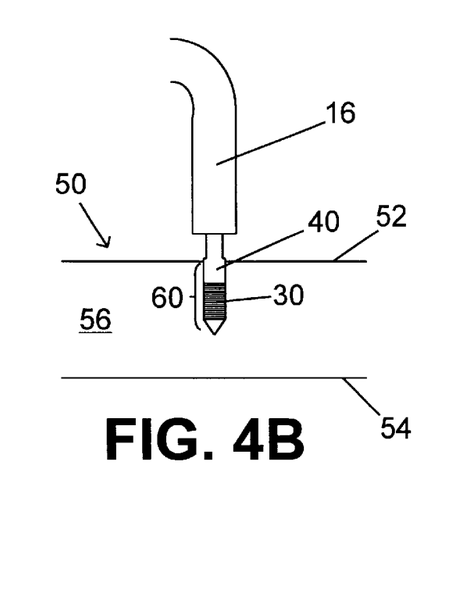

FIG. 4B shows distal end assembly 14 after it has been placed against heart wall 50 and forcibly pushed into the myocardium 56. During this insertion step, distal end assembly 14 is urged into heart wall 50 to an appropriate depth. According to an illustrative embodiment of the invention, the depth of penetration of distal end assembly 14 into heart wall 50 is approximately 4 mm. Accordingly, portions 60 of heart wall 50 are in direct contact with the entire exposed portion 44 of heating element 30, and approximately 2 mm of nonconductive sleeve 40. During the insertion step, controller 18 is not supplying radiofrequency energy to heating element 30.

Figure 4C:
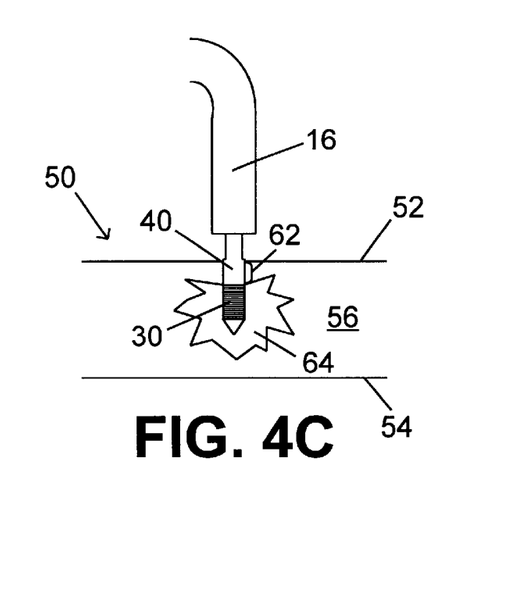

FIG. 4C illustrates a cavity forming step according to an illustrative embodiment of the present invention. During this step distal end assembly 16 is located within the heart wall in accordance with the insertion step, and controller 18, particularly radiofrequency wave form generator 22, supplies a relatively high output of radiofrequency energy to heating element 30 for ablating that portion of myocardium 56 adjacent exposed portion 44 of heating element 30. A portion 62 of myocardium 56 adjacent nonconductive sleeve 40 does not, however, receive the radiofrequency energy from controller 18 and therefore does not ablate. Accordingly, the ablated myocardium adjacent exposed portion 44 of heating element 30 creates a cavity 64 within the myocardium 56. Due to the depth of nonconductive sleeve 40 within the myocardim 56, cavity 64 is formed below surface 52 of heart wall 50. Further, cavity 64 is formed approximately 2 mm below surface 52 of heart wall 50.

Figure 4D:
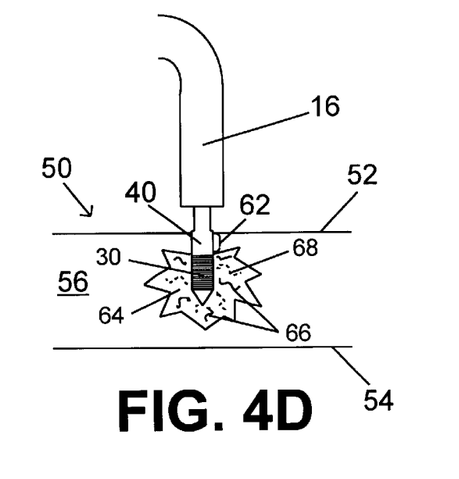

FIG. 4D illustrates an injection step according to the present invention. During this step, a treatment fluid 66, such as the above mentioned growth factor drug, is delivered from the injection assembly 28 (FIG. 1), through hollow guidewire body 16, then through the gaps 32 between coils of heating element 30, and finally into cavity 64 formed in the myocardium 56. Treatment fluid 66 may include, for example, vascular endothelial growth factor (VEGF), fibroblast growth factor (FGF), bone protein (BP), or autologous bone marrow. It is noted that conductor 30 does not receive radiofrequency energy from controller 18 during the injection step.

Figure 4E:
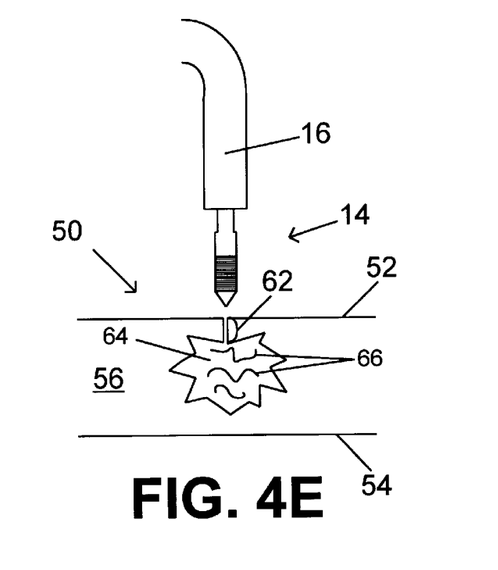

Finally, FIG. 4E illustrates the removal step according to the present invention. During this step, distal end assembly 14 is removed from cavity 64. Upon withdrawal of distal end assembly 14 from heart wall 50, the non-ablated tissue portion 62 forms a restriction or seal over cavity 64. The restriction or seal formed by the non-ablated portion 62 of the heart wall 50 minimizes wash-out of treatment fluid 66 delivered to cavity 64 during the injection step.

In order to further minimize any possibility of wash-out of treatment fluid 66 within cavity 64, a sealing step may be included. This optional step is illustrated in dotted lines in FIG. 4D. The sealing step includes infusing a second fluid or sealing fluid 68 into cavity 64 after delivery of treatment fluid 66. Second fluid 68 is preferably a relatively viscous fluid, or a combination of fluids forming a relatively viscous composition, that further restricts or seals cavity 64. Examples of suitable second fluids include hydrogel precursors. Second fluid(s) 68 may be delivered to the treatment site directly through the same lumen used to inject treatment fluid 66. Alternatively, more than one lumen may be included so that second fluid(s) 68 and treatment fluid 66 are injected independently through different lumens.

According to the method steps described above in connection with FIGS. 4A–4E, an optimum combination of thermal injury and treatment fluid delivery is obtained. The thermal injury associated with the cavity forming step provides the necessary stimulation to promote new blood vessels surrounding the treatment site. Further, the formation of a cavity 64 that can be restricted or sealed allows the most efficient infusion of treatment fluid so that it will not be affected by the powerful contractions of the heart.

Figure 5:
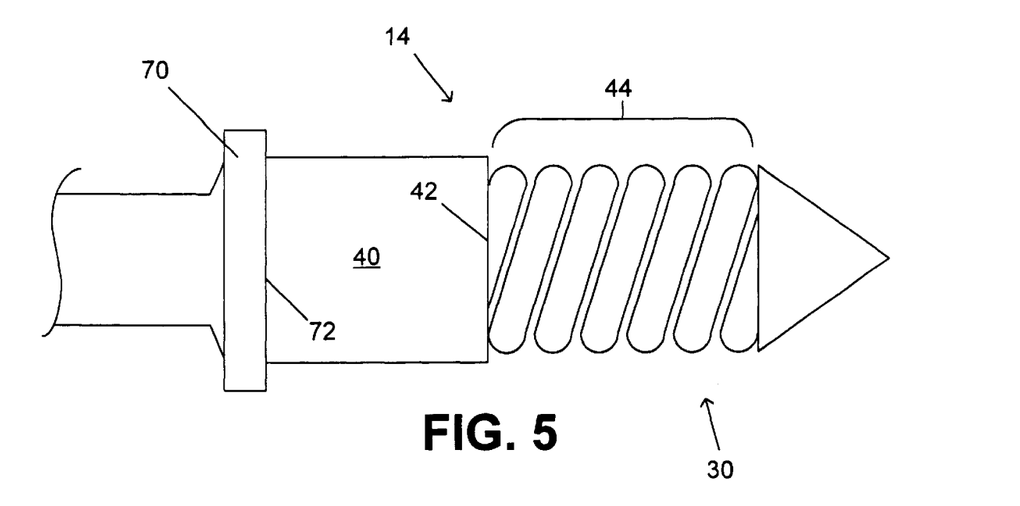
FIG. 5 illustrates an alternative embodiment of the distal end assembly according to the present invention.

In accordance with the device and method steps described above, it is understood that various modifications are available. For example, FIG. 5 illustrates an alternative embodiment of distal end assembly 14. In the alternative embodiment, distal end assembly 14 may be formed with a protrusion or shoulder 70 creating a greater diameter about distal end assembly 14. Protrusion or shoulder 70 is located so that its distal most portion 72 of protrusion or shoulder 70 rests against surface 52 of heart wall 50 when distal end assembly 14 is at a proper depth within heart wall 50. Accordingly, protrusion or shoulder 70 forms a depth guide for inserting end assembly 14 into heart wall 50.

Figure 6:
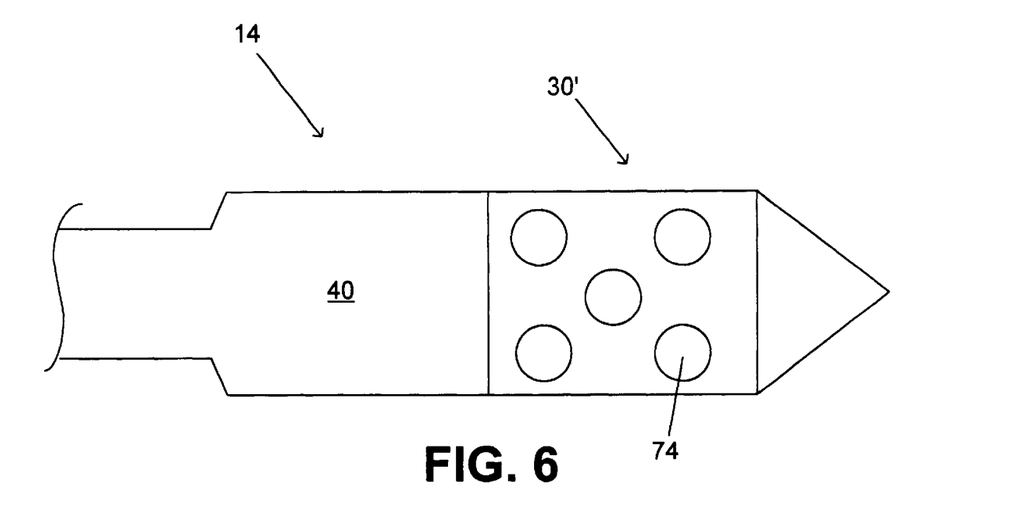
FIG. 6 illustrates an alternative embodiment of the heating element of the distal end assembly according to the present invention.

Further, the coil spring configuration of heating element 30 of distal end assembly 14 could be replaced with another suitable configuration. For example, FIG. 6 illustrates an alternative configuration for heating element 30. According to the alternative configuration of FIG. 6, heating element 30' could be formed in a hollow cylindrical configuration including holes or exit areas 74 therethrough for allowing treatment fluid 66 to flow into cavity 64 formed in heart wall 50.

Further, alternative systems for generating heat at distal end assembly 14 may be used in accordance with this invention. For example, the radiofrequency generator 20 could be replaced with a laser generator or ultrasound generator, and heating portion 44 could be modified to receive the laser or ultrasound energy and transfer it to the treatment site. For example, heating portion 44 could be formed with a hollow body and a laser fiber capable of creating the above described controlled ablation required to form the cavity in the heart wall.

As set forth above, the size of exposed portion 44 of heating element 30 is preferably approximately 2 mm. It is contemplated, however, that the size of exposed portion 44 may be of any size depending upon the diameter of the heating element and the radiofrequency energy supplied. The size of exposed portion 44 must allow enough energy to be supplied to the treatment site to form the desired cavity size without ablating the inner or outer surfaces of the treated wall.

The size of guidewire body 16 and distal end assembly 14 must permit travel through the various passageways and cavities of the patient, and to the desired treatment sites. It is understood, however, that within these size constraints, guidewire body 16 and distal end assembly 14 may be formed of many different sizes according to the desired size and shape of the heart wall cavity formed.

Further, guidewire assembly 10 may be utilized in conjunction with other medical devices. For example, guidewire body 16 may be passed through a guiding catheter or deflectable positioning catheter. Further, as mentioned above, guidewire assembly 10 may be used in association with a navigation or mapping system as disclosed in U.S. Pat. No. 5,443,489 to Ben-Haim and U.S. Pat. No. 5,769,843 to Abela et al.

Figure 7:
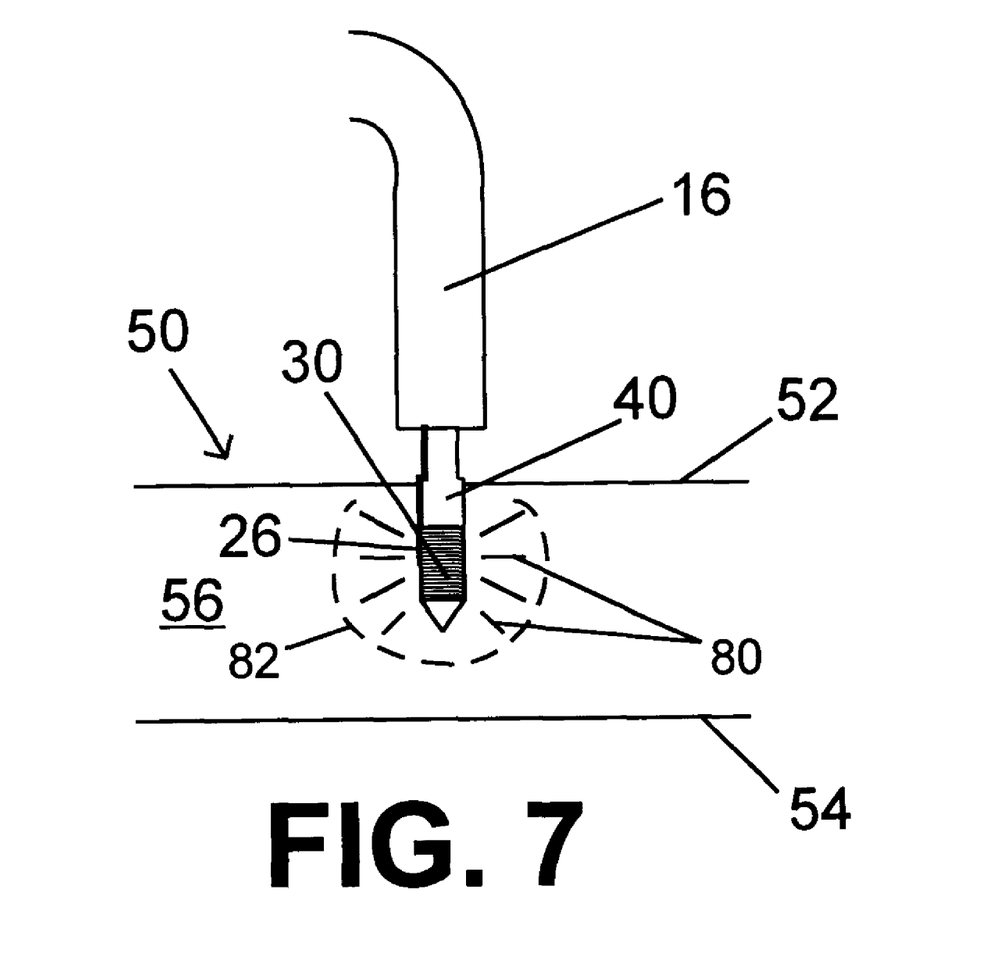
FIG. 7 illustrates a second method for treating tissue according to the present invention.

A second method for treating tissue according to the present invention is illustrated in FIG. 7 and includes creating a controlled injury at the treatment site and then injecting the injury site with a treatment fluid such as a growth factor. The difference between this method and the myocardial revascularization method described above in connection with FIGS. 4A–4E is that the injury inflicted upon the tissue at the treatment site does not causes tissue ablation. For example, it has been found that applying heat 80 at a temperature sufficient to heat the tissue to between 40° C. and 100° C. creates an injury zone 82 that causes reversible cell damage without ablating the tissue. This type of tissue cell damage has been found to enhance the uptake and performance of treatment fluid injected into injury zone 82.

The hollow guidewire system 10 detailed above can be used to carry out the non-ablation heating of tissue. As discussed above, control of the temperature of heating element 30 may be obtained via controller 18 and a thermocouple 24 fixed to heating element 30 (FIG. 1). A microprocessor can be used to continuously monitor the temperature feedback and further adjust the output power to heating element 30 to maintain the temperature within preset limits. Further, the above described methods of injecting fluid through hollow guidewire system 10 may be utilized to inject treatment fluid 66 to injury zone 82.

According to this second method of treating tissue, injury zone 82 may be formed only within the myocardium 56 or may include the epicardium 52 and/or the endocardium 54, or may be formed at a tissue wall of the body other than the heart. Accordingly, nonconductive sleeve 40 detailed above in connection with creating a chamber within the heart wall may or may not be included when practicing this method. Further in accordance with the present invention, injury zone 82 could be created by a heating portion utilizing alternative heat generators, such as a laser heat generator or ultrasound heat generator. The injury zone 82 may also be created by an injury causing assembly including a tissue coring element. Tissue coring element would create injury zone 82 by removing tissue at the treatment site.

As set forth above, the tissue treatment methods detailed above may be performed to promote blood perfusion at treatment sites other than the heart. Alternatively, the methods detailed above may be utilized to retard the growth of certain diseased tissue or tumors. Retarding growth of tissue would be accomplished by the steps set forth above, but with injecting a treatment fluid including an anti-growth factor rather than a growth factor. One example of an anti-growth factor is Angiostatin.

It will be apparent to those skilled in the art that various modifications and variations can be made in the disclosed method and apparatus without departing from the scope or spirit of the invention. Other embodiments of the invention will be apparent to those skilled in the art from consideration of the specification and practice of the invention disclosed herein. For example, the treatment fluid injection aspects of the present invention may be excluded from the device and method detailed above. Without the injection aspects, the only tissue treatment would involve stimulating blood vessel growth in the tissue by creating the above described cavity or injury zone therein. It is intended that the specification and examples be considered as exemplary only, with the full scope of the invention being defined by the following claims.

What is claimed is:

1. A treatment device for body tissue comprising:
   a proximal end assembly including a controller and energy generator; and
   a distal end assembly connected to the proximal end assembly through a body portion, the distal end assembly including a heating portion located distal of a nonconductive portion, the heating portion being operably connected to the controller and energy generator to receive controlled energy therefrom, and the heating portion and nonconductive portion of the distal end assembly are sized so that the heating portion, when inserted into the myocardium of a human heart, is completely located between the epicardium and endocardium and in contact with the surrounding tissue to be ablated, and the nonconductive portion extends through one of the epicardium and endocardium, and includes a proximal boundary allowing the heating portion to be exposed beyond said proximal boundary whereby energy supplied to the heating portion ablates the surrounding myocardium tissue to form a cavity therein while said proximal boundary of the nonconductive portion substantially prevents the ablating of the entry through the epicardium or endocardium to produce a cavity entry with a smaller diameter than the cavity, and the proximal end assembly further includes an injection assembly fluidly connected to the distal end assembly so as to allow fluid to be injected through the distal end assembly and into the cavity formed in the myocardium, the injection assembly including a syringe mechanism, with the body portion including a hollow lumen, and the distal end assembly including a hollow portion and exit areas, so that fluid released from the syringe mechanism travels through the hollow lumen, into the hollow portion of the distal end assembly, through the exit areas, and into the cavity formed in the myocardium, and the distal end assembly includes a heating element in the shape of a coil spring, and the fluid injected into the cavity exits the distal end assembly through gaps in the coil spring.

2. The treatment device according to claim 1, wherein the heating portion of the distal end assembly is approximately two millimeters long.

3. The treatment device according to claim 2, wherein the proximal boundary of the nonconductive portion of the distal end assembly is at least two millimeters long.

4. The treatment device according to claim 1, wherein the distal end assembly includes a heating element having a pointed distal tip, and the nonconductive portion is formed by covering a portion of the heating element with a nonconductive sleeve, while allowing the remaining portion of the heating element to be exposed.

5. The treatment device according to claim 4, wherein the distal end assembly includes a protrusion for limiting the depth of insertion of the heating portion into the myocardium.

6. The treatment device according to claim 4, wherein the energy generator supplies controlled radio requency energy to the heating portion of the distal end assembly.

7. A method for treating tissue within a body comprising the steps of:

inserting a distal end assembly of a tissue treatment device into a tissue wall of the body, said distal end assembly having a heating portion and a nonconductive portion;

providing on said nonconductive portion a proximal boundary allowing insertion into the tissue wall and providing a protective distance between the tissue wall and said heating portion; and forming a cavity completely within surfaces of said tissue wall and a smaller-diameter entry to the cavity through a selected surface of the tissue wall by supplying controlled energy to the heating portion of the distal end assembly, the energy supplied being sufficient to ablate tissue between the surfaces in contact with the heating portion, with the nonconductive portion being positioned to prevent ablation of the selected surface of the tissue wall.

8. The method for treating tissue according to claim 7, wherein the tissue wall is a wall of a human heart.

9. The method for treating tissue according to claim 7, wherein the insertion step includes locating the heating portion within the tissue wall so that a proximal-most portion of the heating portion is approximately two millimeters from a tissue surface from which the heating portion entered the tissue wall.

10. The method for treating tissue according to claim 9, wherein the energy is supplied from one of a radiofrequency generator, an ultrasound generator and a laser generator.

11. The method for treating tissue according to claim 7, further including the step of injecting a treatment fluid from a proximal end of the tissue treatment device through the distal end assembly and into the cavity formed in the tissue wall.

12. The method for treating tissue according to claim 11, wherein the treatment fluid is a tissue growth factor.

13. The method for treating tissue according to claim 11, wherein the treatment fluid is a tissue anti-growth factor.

14. The method for treating tissue according to claim 7, further including the steps of:

injecting a sealing fluid after injection of the treatment fluid, and removing the distal end assembly from the tissue wall, the sealing fluid helping to seal the treatment fluid within the cavity when the distal end assembly is removed from the tissue wall.

15. A method for treating tissue within a body comprising the steps of:

inserting a distal end assembly of a tissue treatment device into a tissue wall of the body, until a heating portion of the distal end assembly is positioned between surfaces of the tissue wall and a nonconducting portion of the distal end assembly is in contact with the selected surface of the tissue wall through which the assembly is inserted;

supplying controlled energy to the heating portion of the distal end assembly to heat the tissue wall to produce within the surfaces of the tissue wall a cavity that is larger than the entry to the cavity through the selected surface by ablating the tissue that is in contact with the heating portion; and injecting a treatment fluid from a proximal end of the tissue treatment device through the distal end assembly and into the cavity in the tissue wall.

16. The method for treating tissue according to claim 15, wherein the tissue wall is a wall of a human heart.

17. The method for treating tissue according to claim 15, further including the step of:

forming a cavity within surfaces of said tissue wall by supplying the controlled energy to the heating portion at a level sufficient to ablate tissue between surfaces of the tissue wall without ablating a surface of the tissue wall.

18. The method for treating tissue according to claim 17, wherein the insertion step includes locating the heating portion within the tissue wall so that a proximal-most portion of the heating portion is approximately two millimeters from a tissue surface.

19. The method for treating tissue according to claim 18, wherein the energy is supplied from one of a radiofrequency generator, an ultrasound generator and a laser generator.

20. The method for treating tissue according to claim 15, further including the step of:

forming an injury zone on the tissue wall by supplying the controlled energy to the heating portion at a level sufficient to cause reversible cell damage without ablating the tissue.

21. The method for treating tissue according to claim 20, wherein the heating portion heats the tissue between 40 and 100 degrees Celsius.

* * * * *